(12) United States Patent
Blakeman et al.

(10) Patent No.: US 10,258,704 B2
(45) Date of Patent: *Apr. 16, 2019

(54) STERILIZING USING OZONE

(71) Applicant: Medaco International Health, LLC, Jackson, MI (US)

(72) Inventors: Rex Blakeman, Jackson, MI (US); Travis W. Pearse, Jr., Jackson, MI (US)

(73) Assignee: Medaco International Health, LLC, Jackson, MI (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/995,280

(22) Filed: Jan. 14, 2016

(65) Prior Publication Data

US 2016/0235874 A1 Aug. 18, 2016

Related U.S. Application Data

(60) Provisional application No. 62/116,769, filed on Feb. 16, 2015.

(51) Int. Cl.
*A61L 2/20* (2006.01)

(52) U.S. Cl.
CPC ........... *A61L 2/202* (2013.01); *A61L 2202/14* (2013.01); *A61L 2202/17* (2013.01); *A61L 2202/24* (2013.01)

(58) Field of Classification Search
CPC ...................................................... A61L 2/202
See application file for complete search history.

(56) References Cited

U.S. PATENT DOCUMENTS

| | | | | | |
|---|---|---|---|---|---|
| 5,069,880 | A | * | 12/1991 | Karlson | A61L 2/202 422/186.07 |
| 6,153,111 | A | * | 11/2000 | Conrad | A61L 2/202 210/741 |
| 7,875,173 | B1 | * | 1/2011 | Barnes | A61H 33/14 210/167.1 |
| 8,337,759 | B1 | * | 12/2012 | Alford | C02F 1/78 422/120 |
| 8,414,839 | B1 | * | 4/2013 | Barnes | A61H 33/14 422/186.12 |
| 2004/0022673 | A1 | * | 2/2004 | Protic | A61L 2/20 422/28 |
| 2005/0031486 | A1 | * | 2/2005 | Mole | A61L 2/202 422/28 |
| 2005/0274663 | A1 | * | 12/2005 | Roitman | B01D 5/0072 210/252 |
| 2009/0311138 | A1 | * | 12/2009 | Klaptchuk | A61L 2/202 422/30 |

(Continued)

*Primary Examiner* — Regina M Yoo
(74) *Attorney, Agent, or Firm* — Honigman LLP

(57) ABSTRACT

The invention relates to a sterilizers and methods of sterilization of an instrument. The sterilizer includes an ozone generator, an air mover, an oxygen concentrator, and a controller. The ozone generator, which is housed by the sterilization chamber, generates at least one plasma field. The air mover circulates air through the sterilization chamber. The oxygen concentrator delivers oxygen-concentrated air to the sterilization chamber. The controller communicates with the ozone generator, the air mover, and the oxygen concentrator. The sterilizer may also include a battery to power the components of the sterilizer. A portable case may house the sterilizer.

19 Claims, 13 Drawing Sheets

(56) References Cited

U.S. PATENT DOCUMENTS

| | | | | |
|---|---|---|---|---|
| 2010/0054989 A1* | 3/2010 | Benedek | ............... | A23B 7/144 422/4 |
| 2010/0178196 A1* | 7/2010 | Garner | ............... | A61L 2/10 422/4 |
| 2010/0228183 A1* | 9/2010 | Sunnen | ............... | A61B 5/412 604/25 |
| 2012/0063949 A1* | 3/2012 | Jennings | ............... | A61L 2/202 422/3 |
| 2012/0198862 A1* | 8/2012 | Arrigo | ............... | A23B 7/148 62/78 |
| 2014/0033445 A1* | 2/2014 | Daniels | ............... | D06F 33/02 8/137 |
| 2014/0193294 A1* | 7/2014 | Kain | ............... | A61L 2/24 422/3 |
| 2014/0338373 A1* | 11/2014 | Arrigo | ............... | F25D 17/042 62/62 |
| 2014/0342064 A1* | 11/2014 | Arrigo | ............... | A23B 7/152 426/312 |

\* cited by examiner

STERILIZING USING OZONE

CROSS REFERENCE TO RELATED APPLICATIONS

This U.S. patent application claims priority under 35 U.S.C. § 119(e) to U.S. Provisional Application 62/116,769, filed on Feb. 16, 2015, which is hereby incorporated by reference in its entirety.

TECHNICAL FIELD

This disclosure relates to methods and apparatuses for sterilizing an object using ozone.

BACKGROUND

Sterilization generally entails the elimination of microbiological organisms to achieve asepsis, a sterile microbial environment. Medical professionals generally need and use sterilized equipment for treating patients, so as to avoid preventable infections or complications that may occur when using non-sterilized equipment. The sterilization of medical equipment can be challenging in non-hospital environments (e.g., in the field) or in third world countries that have limited access to power and clean water. Sterilization can generally be achieved by applying heat, chemicals, irradiation, high pressure, and filtration or combinations thereof.

In general, surgical instruments that enter an already aseptic part of the body (such as the bloodstream, or penetrating the skin) should be sterilized to a low sterility assurance level, or SAL. Examples of such instruments include scalpels, hypodermic needles, etc. A commonly used method for sterilization is heat sterilization, such as by an autoclave, sometimes called a converter. Autoclaves commonly use steam heated to 121-134° C. (250-273° F.). To ensure proper sterilization, most autoclaves have meters and charts that record or display pertinent information such as temperature and pressure as a function of time. Autoclaves, while effective, can be relatively slow and require routine cleaning. Further, autoclaves should not be overcrowded to allow even penetration of steam and are therefore limited as to the number of instruments that can be sterilized at any given time.

SUMMARY

A sterilizing system may include a sterilization chamber, an ozone generator in pneumatic communication with the sterilization chamber, and a controller in communication with ozone generator. The ozone generator may utilize a cold plasma method to generate ozone for sterilizing an object received in the sterilization chamber. The controller may control operation of the ozone generator. The system may optionally include an oxygen concentrator in pneumatic communication with the sterilization chamber that feeds air rich in diatomic oxygen molecules into the sterilization chamber. The diatomic oxygen rich air aids ozone generation through the cold plasma method. The system may also optionally include an air mover arranged to circulate air through the sterilization chamber. The controller may control the oxygen concentrator and the air mover and coordinate operation of its controlled components to achieve a threshold ozone level within the sterilization chamber. The controller, ozone generator, oxygen concentrator, and air mover may receive power from an external power source or a power source integral within the sterilization system. A portable case may house all of the components of the sterilization system, allowing portability and use of the sterilization system in remote locations.

One aspect of the disclosure provides a sterilizer that includes a sterilization chamber, an ozone generator, an air mover, an oxygen concentrator, and a controller. The sterilization chamber houses the ozone generator. The ozone generator generates at least one plasma field in the sterilization chamber. The air mover is in fluid communication with the sterilization chamber and circulates air through the sterilization chamber. The oxygen concentrator is in fluid communication with the sterilization chamber and delivers oxygen-concentrated air to the sterilization chamber. The controller is in communication with the ozone generator, the air mover, and the oxygen concentrator.

Implementations of the disclosure may include one or more of the following optional features. In some implementations, the sterilizer may further include a power source. The power source is in electrical communication with the ozone generator, the air mover, the oxygen concentrator, and the controller. Additionally, the sterilizer may further include a timer used to activate and deactivate at least one of the ozone generator, the air mover, or the oxygen concentrator to maintain a threshold ozone level within the sterilization chamber. In some examples, the controller controls ozone generation to maintain a threshold ozone level of about 4,000 parts per million within the sterilization chamber. This control may be accomplish by pulsing power feed to the ozone generator, maintaining an air recirculation rate of the air mover between about four liters per minute and about six liters per minute, and maintaining an oxygen concentration of the oxygen concentrator of at least seventy-five percent.

In some implementations, the controller includes a toggle switch that controls activation and deactivation of at least one of the ozone generator, the air mover, or the oxygen concentrator. A utensil tray may be removably housed by the sterilization chamber. In some examples, the sterilizer includes an ozone meter in communication with the controller that measures an ozone concentration in the sterilization chamber. Additionally, the sterilizer may further include one or more of an oxygen meter in communication with the controller that measures an oxygen concentration in the sterilization chamber, an oxygen meter in communication with the controller that measures an oxygen concentration of the oxygen-concentrated air delivered by the oxygen concentrator, and an air flow meter in communication with the controller that measures a flow rate of the air circulated by the air mover. Implementations of the disclosure may further include a display. The display is in communication with the controller. Additionally, the display displays information associated with the operation of the sterilizer.

In some implementations, the sterilizer includes one or more spray nozzles, a pump, and a fluid reservoir. The one or more spray nozzles are located in the sterilization chamber. The pump is in fluid communication with one or more spray nozzles, and the fluid reservoir is in fluid communication with the pump. In some examples, the fluid reservoir is in fluid communication with the sterilization chamber and the pump circulates a rinse fluid between the fluid reservoir and the sterilization chamber.

The sterilizer may further include a valve. The valve is in fluid communication with the air mover. Additionally, the valve moves between a closed state and an open state. When the valve is in an open state, the valve directs ozone generated by the ozone generator to the fluid reservoir. In some examples, the valve includes a valve body and a valve seat. The valve body defines a port. The valve seat is located in the valve body. Additionally, the valve seat moves between a closed position seated against the port and an open position spaced from the port when the port receives a connector stud.

In some implementations, the sterilizer includes a rinsing chamber, one or more spray nozzles, a pump, and a fluid reservoir. The one or more spray nozzles are located in the rinsing chamber. The pump is in fluid communication with one or more spray nozzles. The fluid reservoir is in fluid communication with the pump. In some examples, the fluid reservoir is in fluid communication with the rinsing chamber and the pump circulates a rinse fluid between the fluid reservoir and the rinsing chamber.

In some implementations, the sterilizer includes an exhaust meter. The exhaust meter is in fluid communication with the sterilizer chamber and in electrical communication with the controller. Additionally, the exhaust meter measures at least one of an exhaust flow of gas out of the sterilization chamber or an ozone concentration of the exhaust flow of gas. The controller triggers an alarm when the ozone concentration of the exhaust flow of gas is greater than a threshold ozone concentration. The sterilizer may further include a case that houses the sterilization chamber, the air mover, the oxygen concentrator, and the controller.

Another aspect of the disclosure provides a method of sterilizing an instrument. The method includes receiving an instrument in a sterilization chamber and generating at least one plasma field in the sterilization chamber using an ozone generator. The ozone generator is located in the sterilization chamber. The at least one plasma field generates ozone by interacting with Oxygen in the sterilization chamber. The method also includes delivering oxygen-concentrated air to the sterilization chamber and circulating the ozone within the sterilization chamber.

This aspect may include one or more of the following optional features. In some implementations, the method further includes ceasing sterilization after a threshold period of time by ceasing generation of the at least one plasma field, ceasing delivery of oxygen-concentrated air to the sterilization chamber, and/or ceasing circulation of the ozone within the sterilization chamber. In addition, the method may further include measuring an ozone level within the sterilization chamber and triggering an alarm when the ozone level drops below a threshold ozone level before ceasing sterilization.

In some examples, the method includes delivering ozone from the sterilization chamber to a water reservoir. Additionally or alternatively, the method may further include spraying a rinse fluid on the received instrument within the sterilization chamber. The method may further include recirculating the rinse fluid between a fluid reservoir and the sterilization chamber. Moreover, the method may include delivering ozone from the sterilization chamber to the fluid reservoir to sterilize the rinse fluid.

In some examples, the method includes receiving the instrument in a rinsing chamber and spraying a rinse fluid on the received instrument within the rinsing chamber. Additionally, the method may include recirculating the rinse fluid between the fluid reservoir and the rinsing chamber. The method may further include delivering ozone from the sterilization chamber to the fluid reservoir to sterilize the rinse fluid.

In some implementations, the method includes generating at least 4,000 parts per million of ozone within the sterilization chamber. Additionally or alternatively, the method includes circulating the ozone within the sterilization chamber at a rate of about five liter per minute. The method may further include delivering oxygen-concentrated air to the sterilization chamber at a rate of about 1.5 liter per minute. The air delivered to the sterilization chamber has an oxygen concentration of at least seventy-five percent. In some implementations, the method includes exhausting air from the sterilization chamber at a rate of about 0.5 liters per minute.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
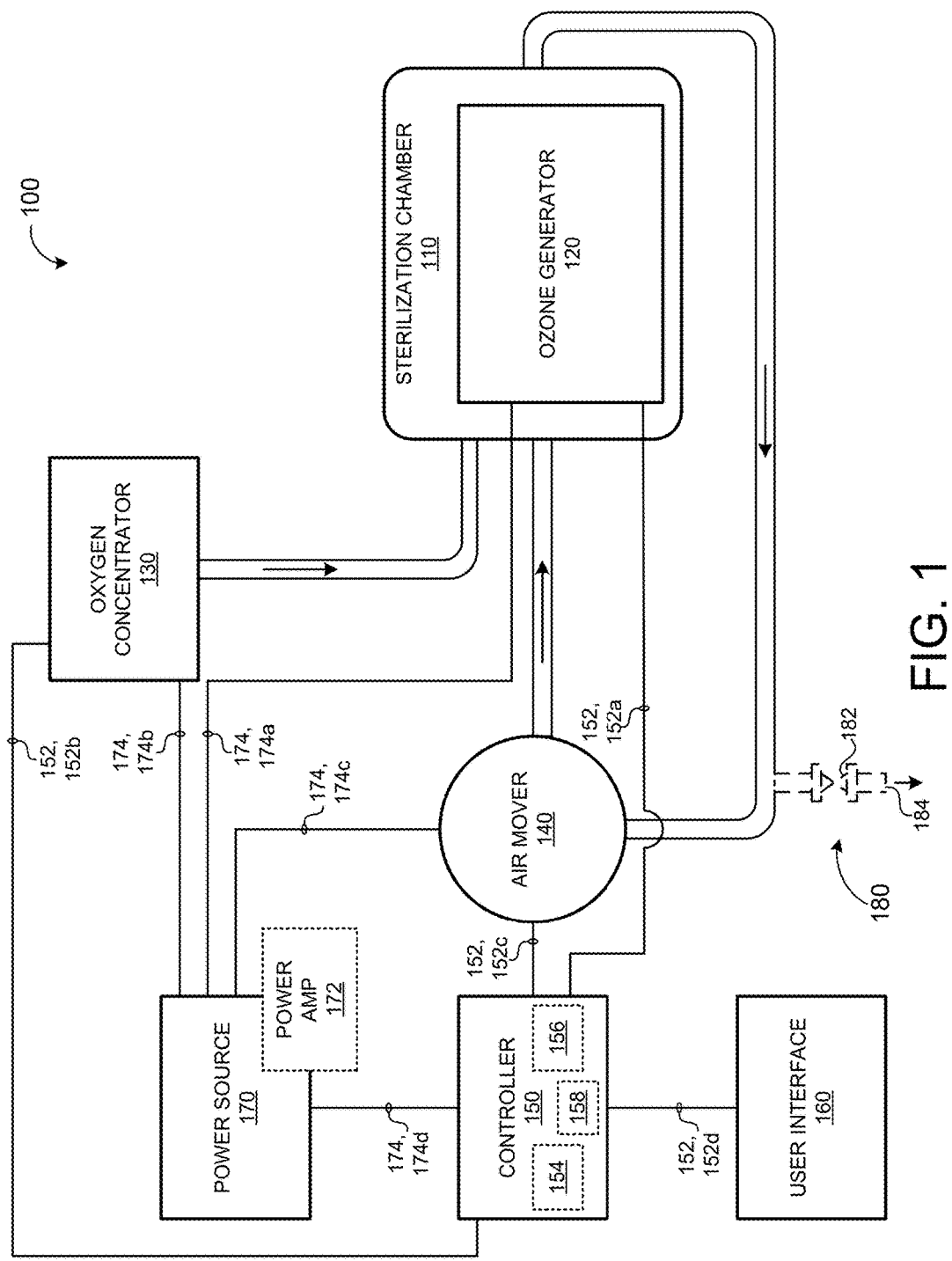
FIG. 1 is a schematic view of an example sterilization system.

Referring to FIG. 1, a sterilization system 100 includes a sterilization chamber 110 housing an ozone generator 120. The ozone generator 120 produces ozone within the sterilization chamber 110 utilizing a cold plasma process, ultra violet light, a corona discharge, or an electrolytic ozone generation process (i.e., a process that splits water molecules into hydrogen ($H_2$), oxygen ($O_2$), and ozone ($O_3$)). While the ozone generator 120 is described as using one of the foregoing processes, the ozone generator 120 may employ any suitable process that generates ozone.

The ozone generator 120 includes an ozone-producing card (FIG. 2) that, when energized, maintains a dielectric barrier discharge for the creation of a plasma field when generating ozone via a cold plasma process. When oxygen-concentrated air is exposed to a plasma field, the plasma splits the diatomic oxygen molecules into oxygen atoms, which then recombine in triplets to form ozone. While the ozone generator 120 may employ any of the processes disclosed above, the cold plasma process has the advantage of quickly producing greater quantities of ozone when compared to the other ozone generation processes.

The sterilization chamber 110 is in fluid communication with an oxygen concentrator 130. The oxygen concentrator 130 produces oxygen-concentrated air, which travels to the sterilization chamber 110. The ozone generator 120 utilizes the oxygen-concentrated air to generate ozone via the cold plasma process described above.

The sterilization chamber 110 is also in fluid communication with an air mover 140. The air mover 140 exhausts air from the sterilization chamber 110 and recirculates the exhausted air through the sterilization chamber 110.

The sterilization system 100 includes a controller 150 in communication with the ozone generator 120, the oxygen concentrator 130, and the air mover 140. In some implementations, the controller 150 includes a timer 154 that automatically terminates operation of the sterilization system 100 after a threshold period of time by directing the ozone generator 120 to cease plasma field generation, directing the oxygen concentrator 130 to cease production of air concentrated with diatomic oxygen molecules, and directing the air mover 140 to cease recirculation of the air within the sterilization chamber 110. The controller 150 may additionally or alternatively include a processor 156 that controls multiple aspects of the sterilization process, including process initiation and termination and memory 158 for storing operational characteristics such as software and/or threshold operating parameters of the sterilization system 100.

The controller 150 communicates with the ozone generator 120 through communication line 152a to control aspects of the plasma field generation and communicates with the oxygen concentrator 130 through a communication line 152b to control aspects of the oxygen-concentrated air production. The controller 150 additionally communicates with the air mover 140 through a communication line 152c to control aspects of the air recirculation process. While the controller 150 is shown as being connected to the various components 120, 130, 140 via communication lines 152a, 152b, 152c, the controller 150 could additionally or alternatively be in communication with the components 120, 130, 140 via a wireless connection.

The sterilization system 100 optionally includes a user interface 160 in communication with the controller 150 through a communication line 152d. Again, while the controller 150 is described and shown as being in communication with the user interface 160 via a communication line, the controller 150 could alternatively be in communication with the user interface 160 via a wireless connection. The user interface 160 may allow the user to control some aspects of the sterilization process such as, for example, process initiation. When the controller 150 includes a timer 156, the user interface 160 may allow a user to set a threshold process time. Alternatively, the controller 150 may prevent a user from adjusting a threshold period of time at the user interface 160 or otherwise to ensure that the system 100 is not operated for a period of time greater than a predetermined threshold period of time.

A power source 170 supplies power to the components of the sterilization system 100 through power lines 174. The ozone generator 120 receives power from the power source 170 through power line 174a. When the sterilization system 100 utilizes the cold plasma process to generate ozone, a power amplifier 172 amplifies the power from the power source 170, along a first power line 174a, to a level suitable for use by the ozone generator 120.

The power source 170 also supplies power to the oxygen concentrator 130 through a second power line 174b, to the air mover 140 through a third power line 174c, and to the controller 150 through a fourth power line 174d. If the system 100 includes a user interface 160, the power source 170 may supplies power to the user interface 160 as well.

The sterilization system 100 optionally includes an exhaust system 180 that is designed to exhaust air from the sterilization chamber 110 through an ozone exhaust port 184. An exhaust valve 182 may control air flow to the ozone exhaust port 184.

Figure 2:
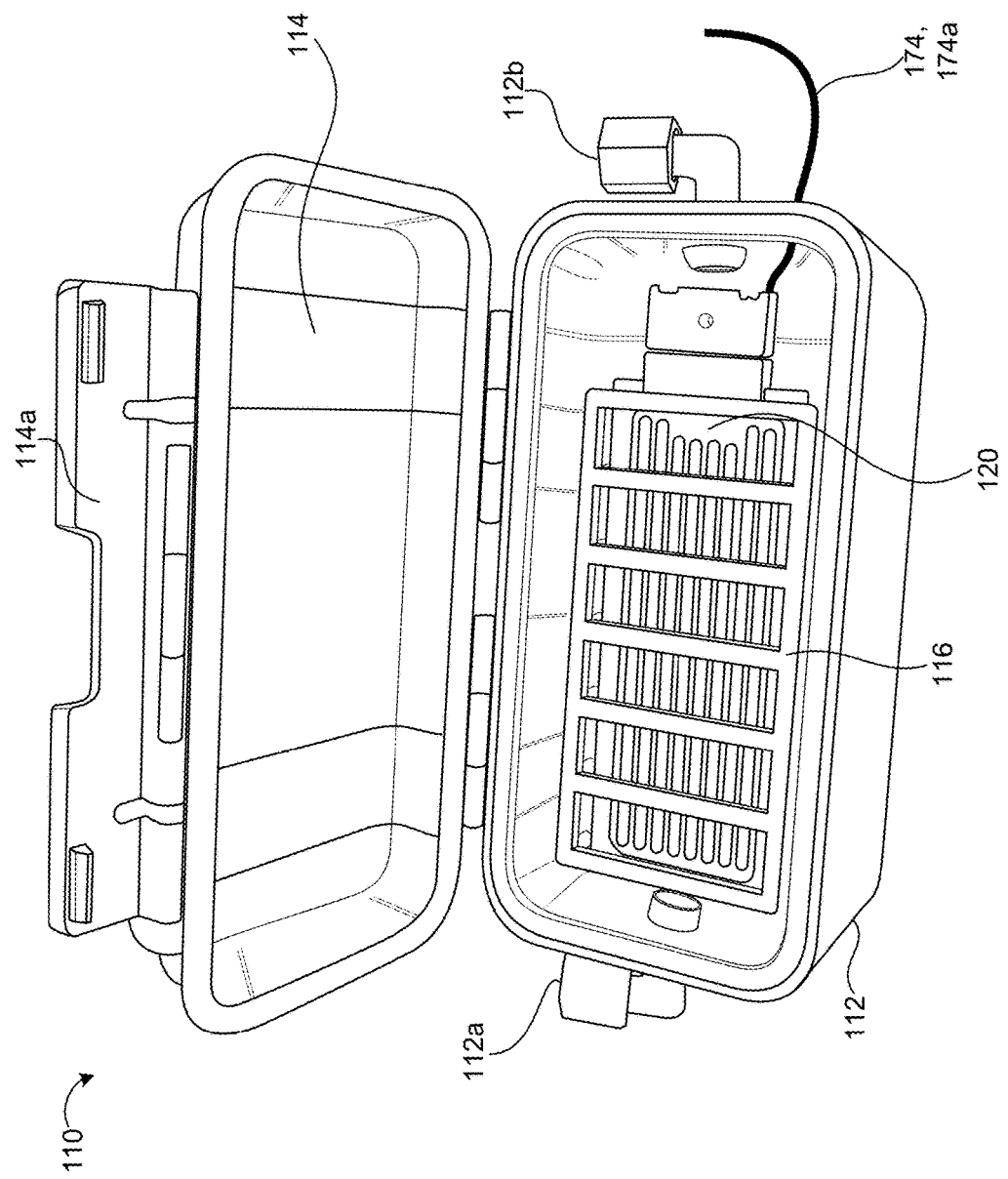
FIG. 2 is a perspective view of an example sterilization chamber housing an ozone generator.

FIG. 2 illustrates an exemplary sterilization chamber 110, which includes a body 112 and a lid 114 received by the body 112. While the lid 114 is illustrated in FIG. 2 as being pivotally coupled to the body 112, the lid 114 may utilize an alternative design; it may be slidably attached to the body 112, uncoupled (e.g., freely attachable and removable from the body 112), or otherwise configured to move between a closed position and an open position. In the closed position, the sterilization chamber 110 may provide the sterilization chamber 110 with a hermetic seal to prevent escapement of ozone from the sterilization chamber 110. The lid 114 may be locked in the closed position during operation of the ozone generator 120 (e.g., during a sterilization process) using a locking mechanism 114a to prevent inadvertent or premature opening of the sterilization chamber 110 by a user. Additionally, the locking mechanism 114a may serve to draw the lid 114 closer to the body 112, thereby improving the seal between the body 112 and the lid 114 and reducing the likelihood that ozone will escape the chamber 110. Alternatively, the lid 114 of the sterilization chamber 110 may be provided without a locking mechanism 114a.

The sterilization chamber 110 houses a utensil tray 116. In operation, a user deposits an instrument or utensil to be sterilized (not shown) into the utensil tray 116 and closes the lid 114 of the sterilization chamber 110. Once the sterilization process has begun, the ozone generated by the ozone generator 120 sterilizes the instrument or utensil in the utensil tray 116.

The sterilization chamber 110 houses the ozone generator 120. The ozone producing card discussed above may include a first plate and a second plate (neither shown), which are energized by the power source 170 through the first power line 174a. The first plate and the second plate are constructed of stainless steel or another suitable material for transferring electrons between the plates and producing a plasma field when the power source 170 provides the plates with a voltage. A dielectric layer is positioned between the first plate and the second plate that maintains an even distribution of the electron transfer and prevents arcing.

The ozone producing card generates a plasma field when the power source 170 provides an input voltage through the first power line 174a. The applied voltage causes a current to be applied across both the top plate and the bottom plate, thereby producing plasma fields. Any voltage sufficient to power the ozone generator 120 may be utilized. For example, an input of approximately +3,500 V DC across the first plate and approximately −3,500 V DC across the second plate may be used to power the ozone generator 120.

The controller 150 optionally times the ozone generation and may turn the ozone generator 120 on and off at preset time intervals to pulse the discharge of the plasma fields. The controller 150 accomplishes this by pulsing the power feed from the power source 170 to the ozone generator 120.

The air mover 140 circulates gas into the sterilization chamber 110 at the gas inlet 112a, through the sterilization chamber 110, and out of the sterilization chamber 110 at the gas outlet 112b. The gas entering the sterilization chamber 110 at the gas inlet 112a comprises a combination of the gas exhausted from the gas outlet 112b of the sterilization chamber 110 and gas concentrated with diatomic oxygen molecules produced by the oxygen concentrator 130. The continuous supply of this mixture maintains an elevated oxygen concentration within the sterilization chamber 110.

The concentrated oxygen within the sterilization chamber 110 contacts the plasma fields generated by the ozone generator 120. Upon contact, the diatomic oxygen molecules are split into oxygen atoms. The split oxygen atoms combine in groups of three oxygen atoms to form ozone within the sterilization chamber 110. Driven by the oxygen-concentrated air entering the sterilization chamber 110 through the gas inlet 112a from the oxygen concentrator 130, the ozone generator 120 maintains elevated concentrations of ozone inside the sterilization chamber 110. It is advantageous to maintain a minimum of approximately 4,000 ppm of ozone within the sterilization chamber 110 in order to obtain sufficient sterilization.

Figure 3:
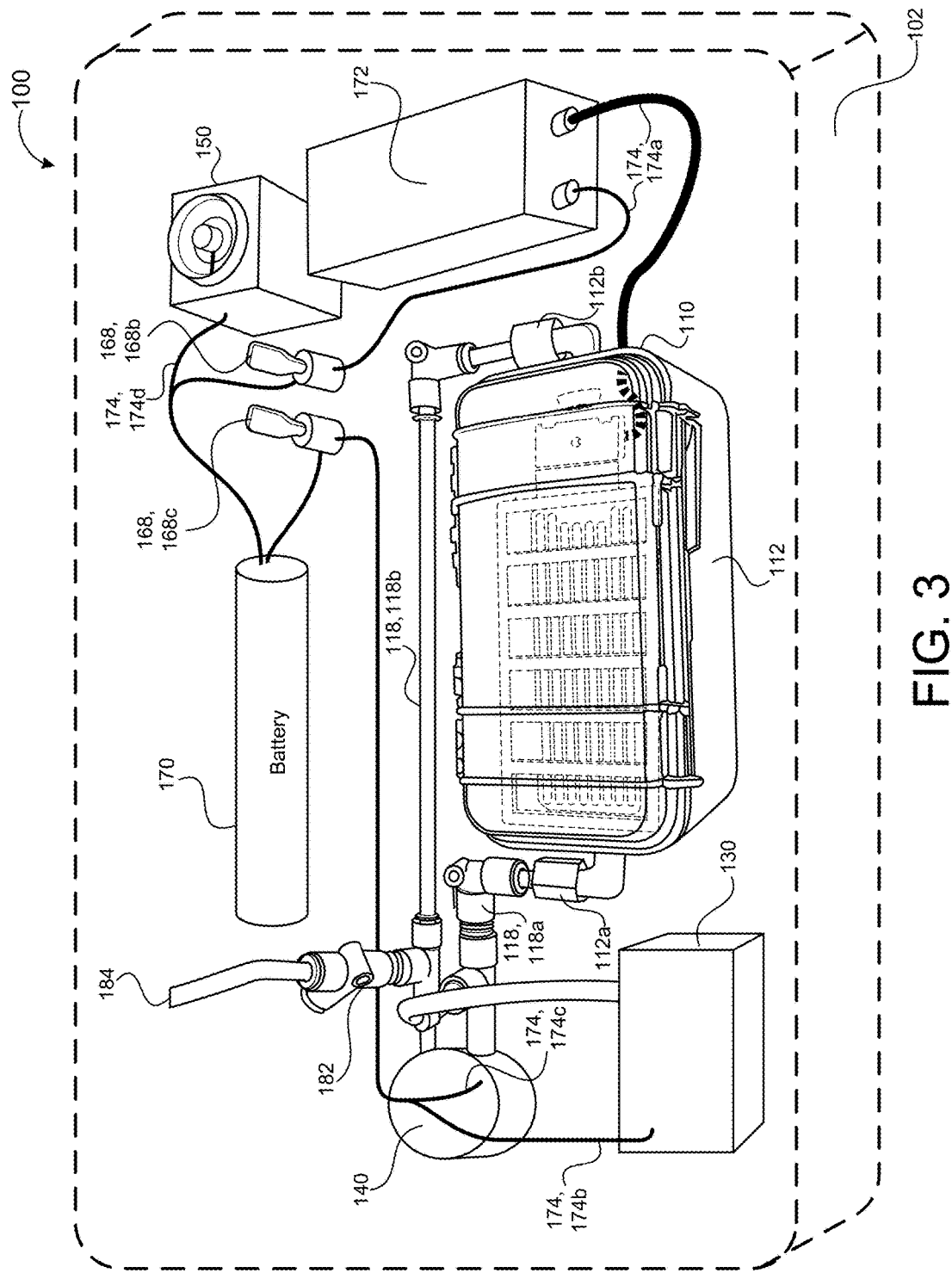
FIG. 3 is a perspective view of an example sterilization system housed within a portable case.

Referring to FIG. 3, a portable case 102 houses the sterilization system 100. The portable case 102 includes a body (not shown) and a lid (not shown) that can be pivotally coupled to the body of the case 102, slidably attached to the body of the case, uncoupled (e.g., freely attachable and removable), or otherwise configured to move between a closed position and an open position. When the lid is in the closed position, a user can easily and securely convey the sterilization unit 100 from one location to another. During times of conveyance, it is advantageous that the portable case 102 maintains the positioning of each component of the sterilization system 100. Accordingly, the various components of the system 100 may be fixed relative to the body of the case 102 such that relative movement between the components of the system 100 and the body of the case 102 is restricted.

Within the portable case 102, the components of the sterilization system 100 are arranged in any manner that permits the system to operate as designed. FIG. 3 illustrates one such exemplary arrangement. This arrangement may be predetermined based on depressions or other location features of the case body that ensure each component of the system 100 is properly installed in a predetermined location within the case 102. In the illustrated configuration, the oxygen concentrator 130 and the air mover 140 are disposed relative to the gas inlet 112a on the body 112 of the sterilization chamber 110.

The gas inlet piping/tubing 118a fluidly connects the oxygen concentrator 130 and the air mover 140 to the gas inlet 112a on the body 112 of the sterilization chamber 110. FIG. 3 illustrates an exemplary implementation in which a single gas inlet 112a receives the output from both the oxygen concentrator 130 and the air mover 140.

The oxygen concentrator 130 produces oxygen-concentrated air and injects the gas into the gas inlet piping/tubing 118a. In the gas inlet piping/tubing 118a, the oxygen-concentrated air combines with the recirculating ozone-concentrated air from the air mover 140. In one configuration, the oxygen concentrator 130 supplies approximately 1.5 liters per minute of gas flow having an oxygen concentration of at least seventy-five percent in order to maintain the ozone concentration at approximately 4,000 ppm in the sterilization chamber 110.

The air mover 140 optionally includes a pneumatic pump or any other mechanical system or device capable of recirculating sufficient quantities of air through the sterilization chamber 110. The air mover 140 is in fluid communication with the gas outlet 112b on the body 112 of the sterilization chamber 110 and extracts ozone-concentrated air from the sterilization chamber 110, which travels through the gas outlet piping/tubing 118b and is either exhausted or is recirculated.

The ozone exhaust port 184 releases from the sterilization system 100 a portion of the ozone-concentrated air, which the air mover 140 extracted from the sterilization chamber 110. An exhaust valve 182 controls the flow rate of this ozone-concentrated air released at the ozone exhaust port 184.

The air mover 140 recirculates the remainder of the extracted ozone-concentrated air into the gas inlet 112a on the body 112 of the sterilization chamber 110. It is advantageous to maintain a recirculation rate of the ozone-concentrated air at approximately five liters per minute in order to maintain the ozone concentration at approximately 4,000 ppm in the sterilization chamber 110.

The portable case 102 also houses the controller 150. In the exemplary implementation of FIG. 3, the controller 150 receives continuous power from the power source 170 through the fourth power line 174d.

In the configuration illustrated in (FIG. 3, the communication lines 152 (shown in FIG. 1) extend within the portable case 102 from the controller 150 to various components of the sterilization system 100 allowing the controller 150 to oversee and/or control various aspects of the sterilization operation. The aspects of the operation overseen and/or controlled by the controller 150 include, but are not limited to, operation initiation and operation termination. For clarity purposes, the communication lines 152 are not shown in FIG. 3.

On/off switches 168 optionally allow a user to selectively turn on and off components of the sterilization system 100. For example, FIG. 3 illustrates an exemplary implementation utilizing one switch 168b to turn on and off the ozone generator 120 and a second switch 168c to turn on and off the oxygen concentrator 130 and the air mover 140.

The power source 170 may include a battery that is disposed within the portable case 102 of the sterilization system 100. In the alternative, the sterilization system 100 can utilize an external power source, which can either be portable or fixed. The first power line 174a from the power source 170 to the ozone generator 120 includes a power amplifier 172 and powers the ozone generator 120. The second power line 174b from the power source 170 powers the oxygen concentrator 130, while the third power line 174c from the power source 170 powers the air mover 140.

Figure 4:
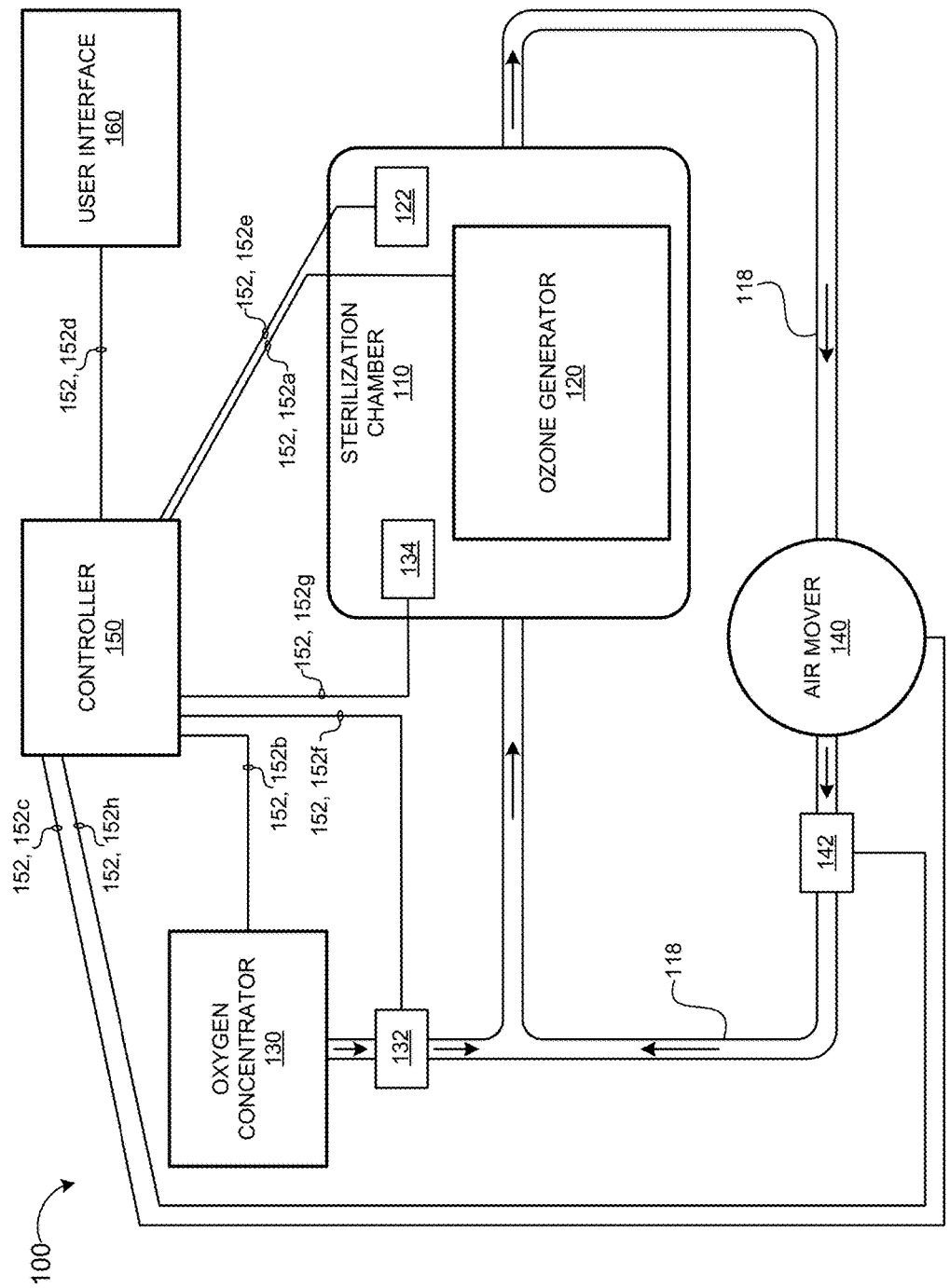
FIG. 4 is a schematic view of an example sterilization system and communication connections therein.

Referring to FIG. 4, the sterilization system 100 is shown as utilizing one or more measuring devices 122, 132, 134, 142. Communication lines 152 send output signals from the one or more measuring devices 122, 132, 134, 142 to the controller 150. The controller may utilize the signals from these one or more measuring devices 122, 132, 134, 142 to display information on the user interface 160 and/or to adjust the operation of other components of the sterilization system 100. The power source 170 is in electrical communication with and powers the one or more measuring devices 122, 132, 134, 142.

The measuring device 122 may be an ozone meter 122 that measures ozone concentrations within the sterilization chamber 110. The ozone meter 122 communicates the ozone concentration to the controller 150 through communication line 152e. The user interface 160 optionally displays the ozone concentration to permit a user to readily ascertain the ozone concentration within the chamber 110. The controller 150 may receive information from the ozone meter 122 regarding the concentration measurements to allow the controller 150 to adjust operation of the various components of the sterilization system 100 such as, for example, the ozone generator 120, the oxygen concentrator 130, and the air mover 140. Such adjustments by the controller 150 aim to implement an increase or decrease to the ozone concentration in the sterilization chamber 110 to maintain the ozone concentration within the chamber 110 at a predetermined concentration (i.e., at or above approximately 4,000 ppm in one configuration).

The measuring device 132 may be an oxygen meter 132 that measures at least one of an air flow rate from the oxygen concentrator 130 or a concentration of diatomic oxygen molecules within the air flowing from the oxygen concentrator 130. The oxygen meter 132 communicates its measurements to the controller 150 through a communication line 152*f*. As with the ozone concentration meter 122, the user interface 160 may display the measurements received from the oxygen meter 132. The controller 150 may receive the measurements from the oxygen meter 132 and may adjust operation of the oxygen concentrator 130 through the communication line 152*b*. The communicated operational changes aim to implement an increase or a decrease of at least one of the air flow rate from the oxygen concentrator 130 or the concentration of diatomic oxygen molecules within the air flowing from the oxygen concentrator 130 to maintain the ozone concentration within the chamber 110 at a predetermined concentration.

The measuring device 134 may be an oxygen concentration meter 134 that measures the concentration of diatomic oxygen molecules within the sterilization chamber 110. The oxygen concentration meter 134 communicates the oxygen concentration to the controller 150 through a communication line 152*g*. Once again, the user interface 160 may display the concentration received from the oxygen concentration meter 134. The controller 150 may utilize the oxygen concentration measurements to adjust operation of the oxygen concentrator 130 through the communication line 152*b*. The communicated operational changes aim to implement an increase or decrease in the concentration of diatomic oxygen molecules within the sterilization chamber 110 to once again maintain the ozone concentration within the chamber 110 at a predetermined concentration.

The measuring device 142 may be an air flow meter 142, which is disposed on the gas piping/tubing 118. The air flow meter 142 measures the air recirculation flow rate through the air mover 140 and communicates the air recirculation flow rate to the controller 150 through communication a line 152*h*. As with the measuring devices 122, 132, 134, the user interface 160 may display the flow rate to communicate the flow rate to the user. The controller 150 may also utilize the flow rate measurements to adjust the speed of the air mover 140 to increase or decrease the flow rate. Specifically, the controller 150 may send a signal to the air mover 140 via the communication line 152*c* to adjust an output of the air mover 140 based on the current ozone concentration in the chamber 110.

As set forth above, the controller 150 receives information from the various measurement devices 122, 132, 134, 142 for use by the controller 150 in controlling the various components 120, 130, 140 of the sterilization system 100 all in an effort to maintain an ozone concentration in the chamber 110 at a predetermined level. The controller 150 may additionally receive various user-inputs to aid or direct the controller 150 in controlling the various components 120, 130, 140. For example, a user may change the desired ozone concentration by adjusting the predetermined value above or below 4000 ppm. The controller 150 may receive this information along with information from the measurement devices 122, 132, 134, 142 and may control the various components 120, 130, 140 based on this information.

An error warning is optionally displayed on the screen 162 of the user interface 160 when any one of the measurements reaches a preset high or low level. An additional or different warning may be displayed when the controller 150 is unable to direct the sterilization system 100 to bring the measurements within the preset levels.

Figure 5:
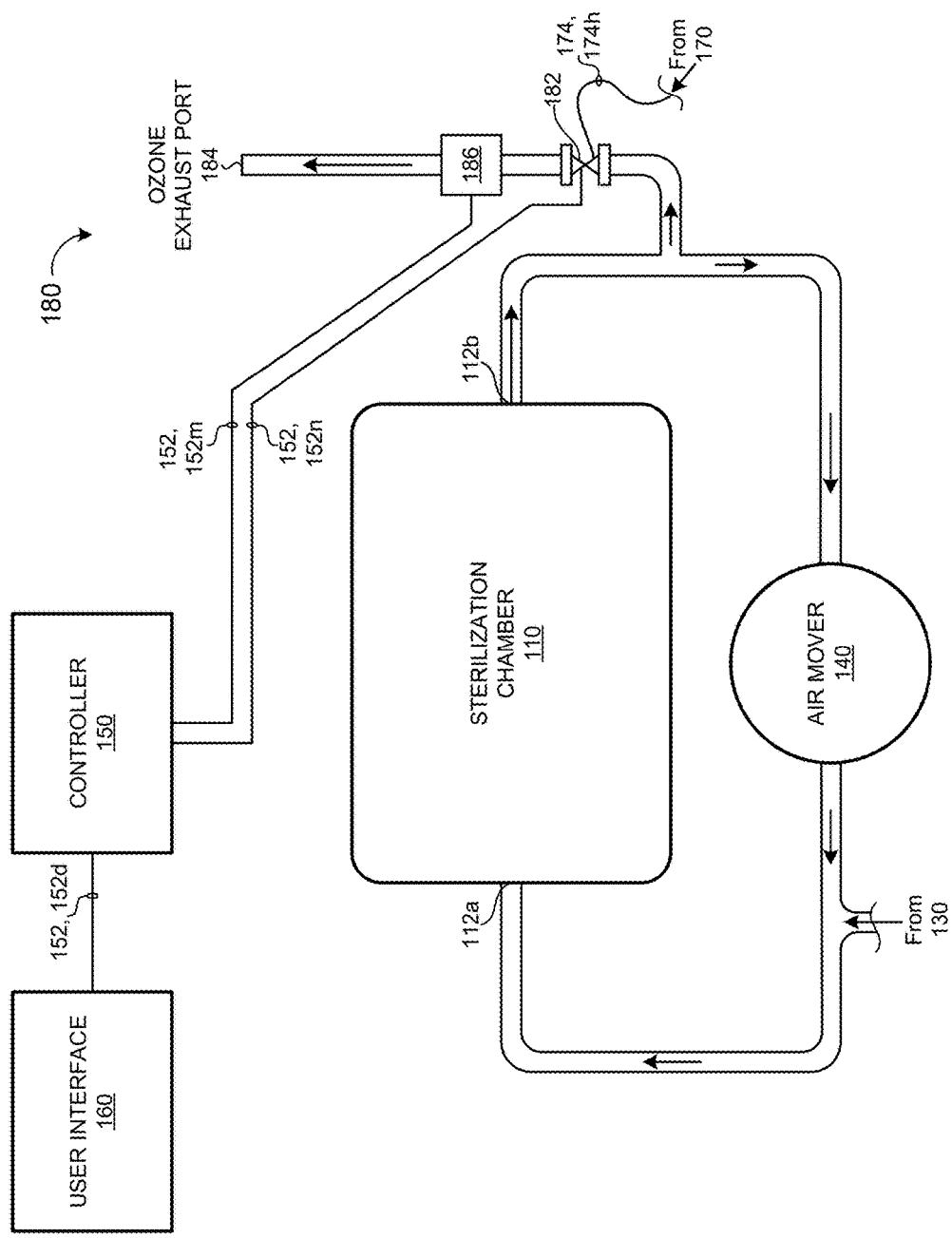
FIG. 5 is a schematic view of an example sterilization system having an exhaust system.

Referring to FIG. 5, in some implementations, an exhaust system 180 releases ozone-concentrated air from the sterilization chamber 110 and the sterilization system 100. The air mover 140 extracts ozone-concentrated air from the gas outlet 112*b* on the body 112 of the sterilization chamber 110. The air mover 140 recirculates a portion of this extracted air back into the sterilization chamber 110 through a gas inlet 112*a*, and the exhaust system 180 exhausts the remainder of the extracted air. The exhausted ozone-concentrated air separates from the recirculated air prior to reaching the air mover 140 and exits the sterilization system 100 at the ozone exhaust port 184.

An exhaust valve 182 optionally controls the flow of the ozone-concentrated air exiting the sterilization system 100 at the ozone exhaust port 184. In the configuration of the exhaust system 180 of FIG. 5, the exhaust valve 182 modulates between fully open and fully closed. An exhaust meter 186, located downstream of the exhaust valve 182, measures the flow of the ozone-concentrated air to the ozone exhaust port 184. In other configurations, the exhaust meter 186 is located upstream of the exhaust valve 182.

The exhaust meter 186 communicates the flow measurement to the controller 150 through a communication line 152*m*. The user interface 160 optionally displays the flow measurement. The controller 150 utilizes the flow measurement to communicate a change in position of the exhaust valve 182 through a communication line 152*n* in order to increase or decrease the flow rate of the ozone-concentrated air to the ozone exhaust port 184. The power source 170 provides power through power line 174*h* for automatic modulation of the exhaust valve 182 and also powers the exhaust meter 186.

Other configurations of the exhaust system 180 do not include an exhaust meter 186. For example, in one such system, the exhaust valve 182 remains open during operation of the sterilization system 100 unless a user manually closes the exhaust valve 182. In another exemplary configuration of the exhaust system 180, the exhaust valve 182 opens and closes as directed by a signal from the controller 150 through communication line 152*n*, but the exhaust valve 182 does not modulate. In this implementation, the power source 170 provides power for automatic opening and closing of the exhaust valve 182.

Whether or not the exhaust system 180 includes an exhaust meter 186, the controller 150 may maintain an exhaust flow rate of ozone-concentrated air at approximately 0.5 liters per minute. Maintaining a flow rate of approximately 0.5 liters per minute relieves excessive pressure that has accumulated within the sterilization chamber 110 and the gas piping/tubing 118.

Figure 6:
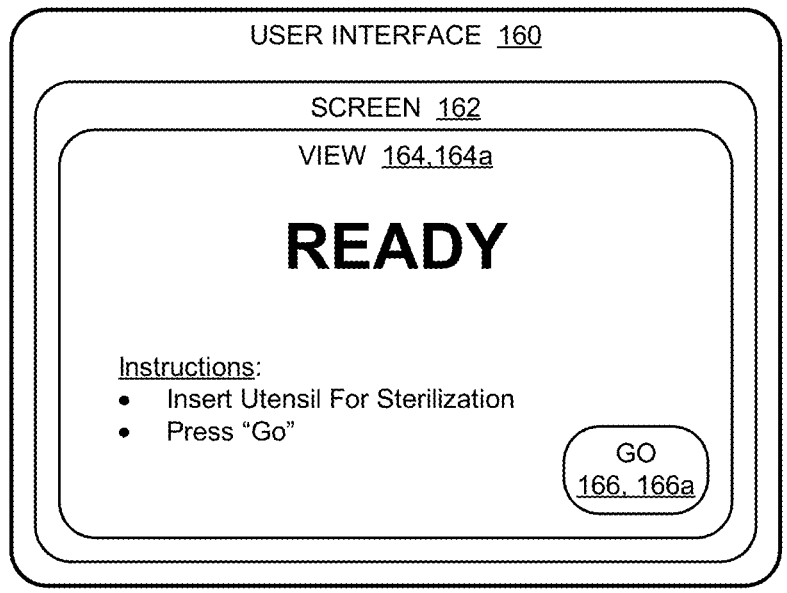
FIGS. 6-9 are schematic views of example user interfaces.

As discussed above, the user interface 160 includes the screen 162 (e.g., liquid-crystal display (LCD), touch display screen, etc.) that displays one or more views 164, each of which optionally includes one or more user interface buttons 166. FIG. 6 illustrates an example ready view 164*a*. The ready view 164*a* includes a 'GO' button 166*a*, which allows the user to initiate operation of the sterilization system 100.

Figure 7:
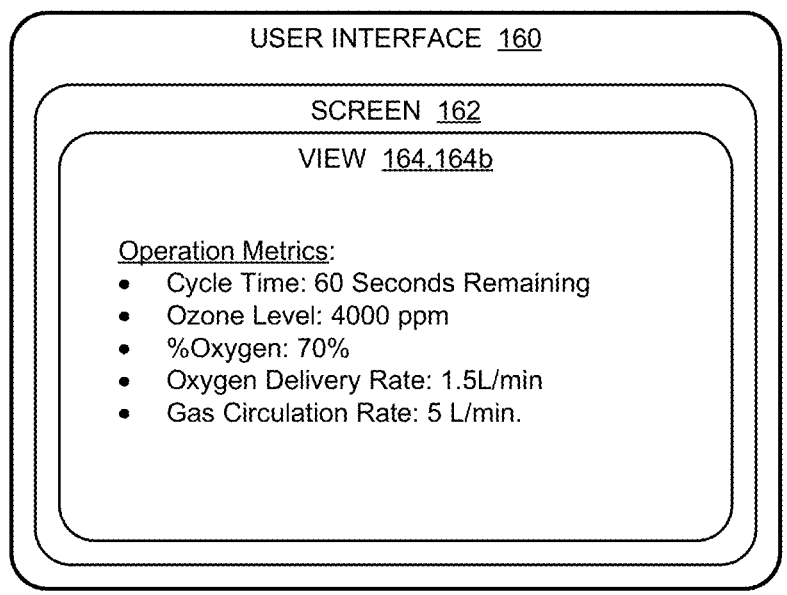

FIG. 7 illustrates an example operation view 164b that includes one or more operation metrics. The operation metrics may include, but are not limited to, a cycle time (e.g., a time remaining in a sterilization cycle), an Ozone level in the sterilization chamber 110, an Oxygen level (e.g., percentage of Oxygen) in the sterilization chamber 110, an Oxygen delivery rate (e.g., in L/min.), and/or a gas recirculation rate (e.g., in L/min.) through the sterilization chamber 110.

Figure 8:
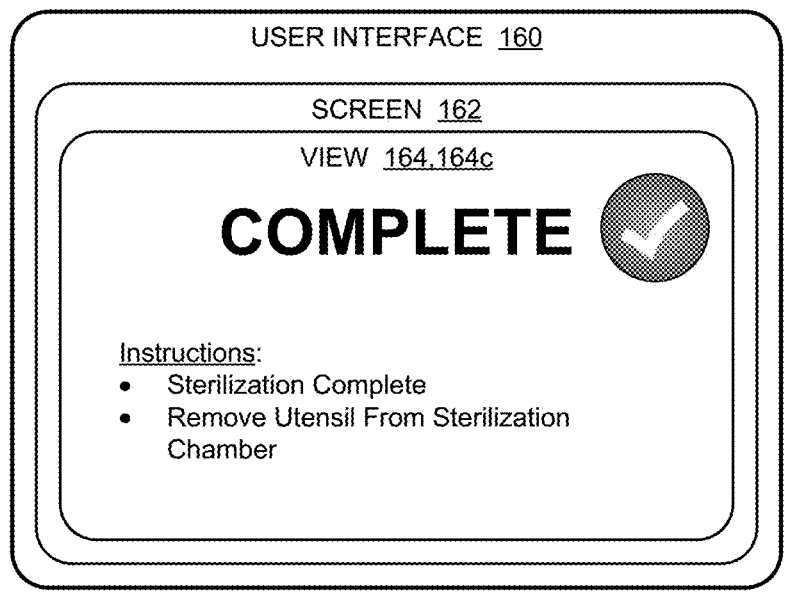

FIG. 8 illustrates an example operation complete view 164c. The operation complete view 164c may include one or more words and/or a glyph indicating to the user that the sterilization operation is complete. Moreover, the operation complete view 164c may include instructions indicating how the user may retrieve the sterilized instrument from the sterilization chamber 110 without compromising the sterilized nature of the instrument.

Figure 9:
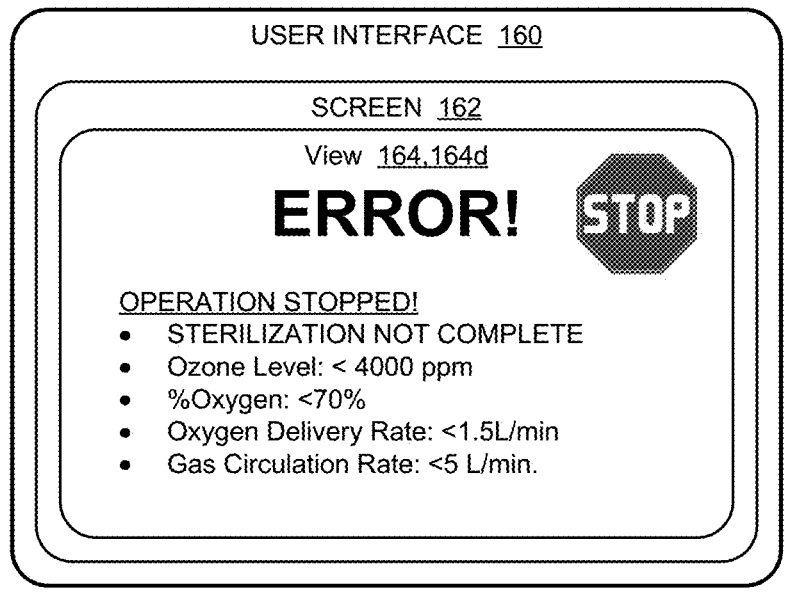

FIG. 9 illustrates an example error view 164d. The error view 164d may include one or more words and/or a glyph indicating to the user that the sterilization operation experienced an error and/or that the sterilization operation is not complete. In the example shown, the error view 164d indicates that the sterilization operation was stopped, that the sterilization operation is not complete, and the operation metrics at the time the operation stopped. Other information can be provided as well or in lieu of that shown in the example.

Figure 10:
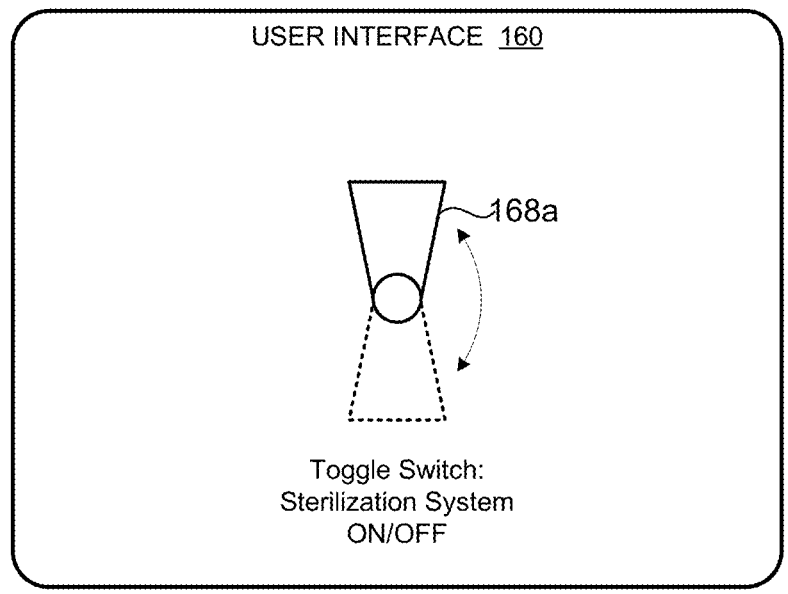
FIG. 10 is a schematic view of an example user interface having a single on/off switch.
Figure 11:
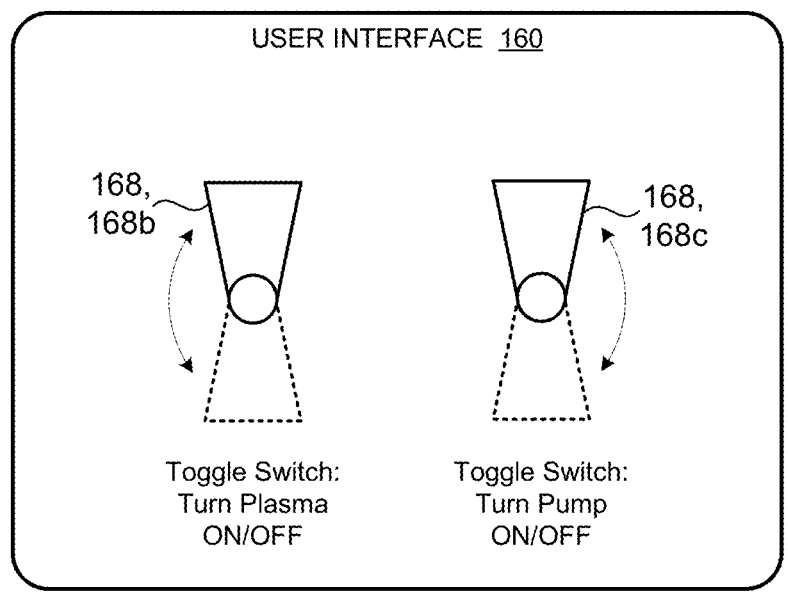
FIG. 11 is a schematic view of an example user interface having two on/off switches.

Referring to FIGS. 10-11, in some implementations, the user interface 160 includes one or more on/off switches 168. FIG. 10 illustrates an example user interface 160 with a single on/off switch 168a to initiate full operation of the sterilization system 100. FIG. 11 illustrates an example user interface 160 with a first on/off switch 168b to initiate operation of the ozone generator 120 and a second on/off switch 168c to initiate operation of the oxygen concentrator 130 and the air mover 140.

Referring to FIGS. 12-16, in some implementations, the sterilization system 100 includes a rinsing system 190. The rinsing system 190 enables the sterilization of a rinse fluid within a fluid reservoir 192 and the application of the sterilized rinse fluid to an instrument or utensil. The application of the sterilized rinse fluid to the instrument or utensil may serve to remove bio burden from the instrument or utensil, sterilize the instrument or utensil, or accomplish both removal of bio burden and sterilization.

Figure 12:
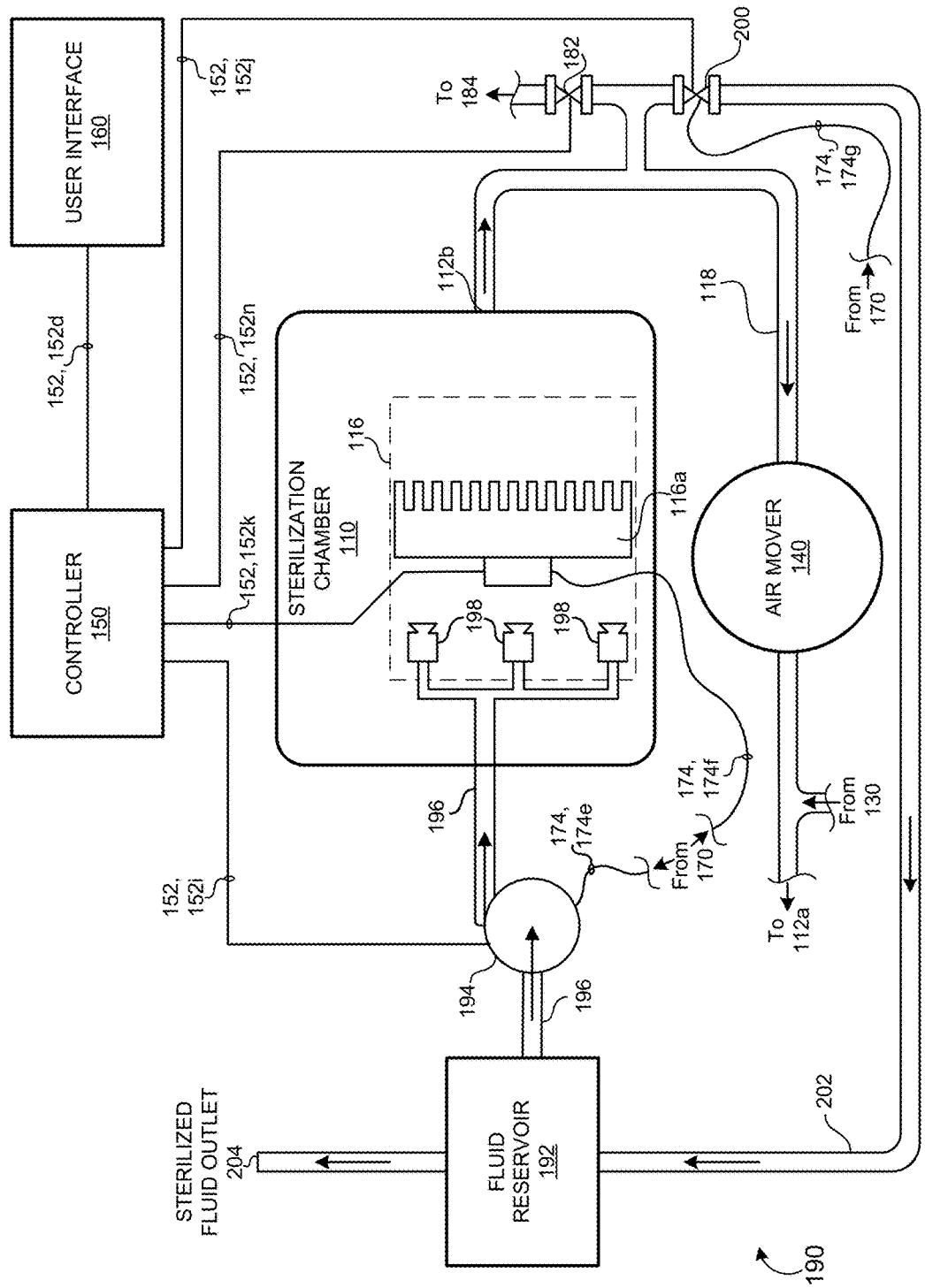
FIG. 12 is a schematic view of an example sterilization system having a pre-wash system.

Referring specifically to FIG. 12, the user simply deposits the instrument or utensil into the utensil tray 116 and closes the lid 114 of the sterilization chamber 110. A rinse fluid pump 194 initiates a flow of rinse fluid through the rinse fluid piping/tubing 196. The rinse fluid enters the sterilization chamber 110, and one or more nozzles 198 spray the rinse fluid at the utensil tray 116 to remove the bio burden from the instrument or utensil. This process may be referred to as a pre-wash cycle. After the rinsing system 190 concludes the pre-wash cycle, the ozone generator 120, oxygen concentrator 130, and air mover 140 commence operation to begin sterilization.

Alternatively, the implementation of the rinsing system 190 illustrated in FIG. 12 may be utilized to apply the rinse fluid after the sterilization process utilizing the ozone-concentrated air has occurred within the sterilization chamber 110. In this case, the rinsing system 190 applies to sterilized fluid to effectuate additional sterilization of the instrument or utensil. This utilization of the rinsing system 190 may prove desirable because, under some conditions, ozone-concentrated fluid allows for more effective sterilization than ozone-concentrated air.

Figure 13:
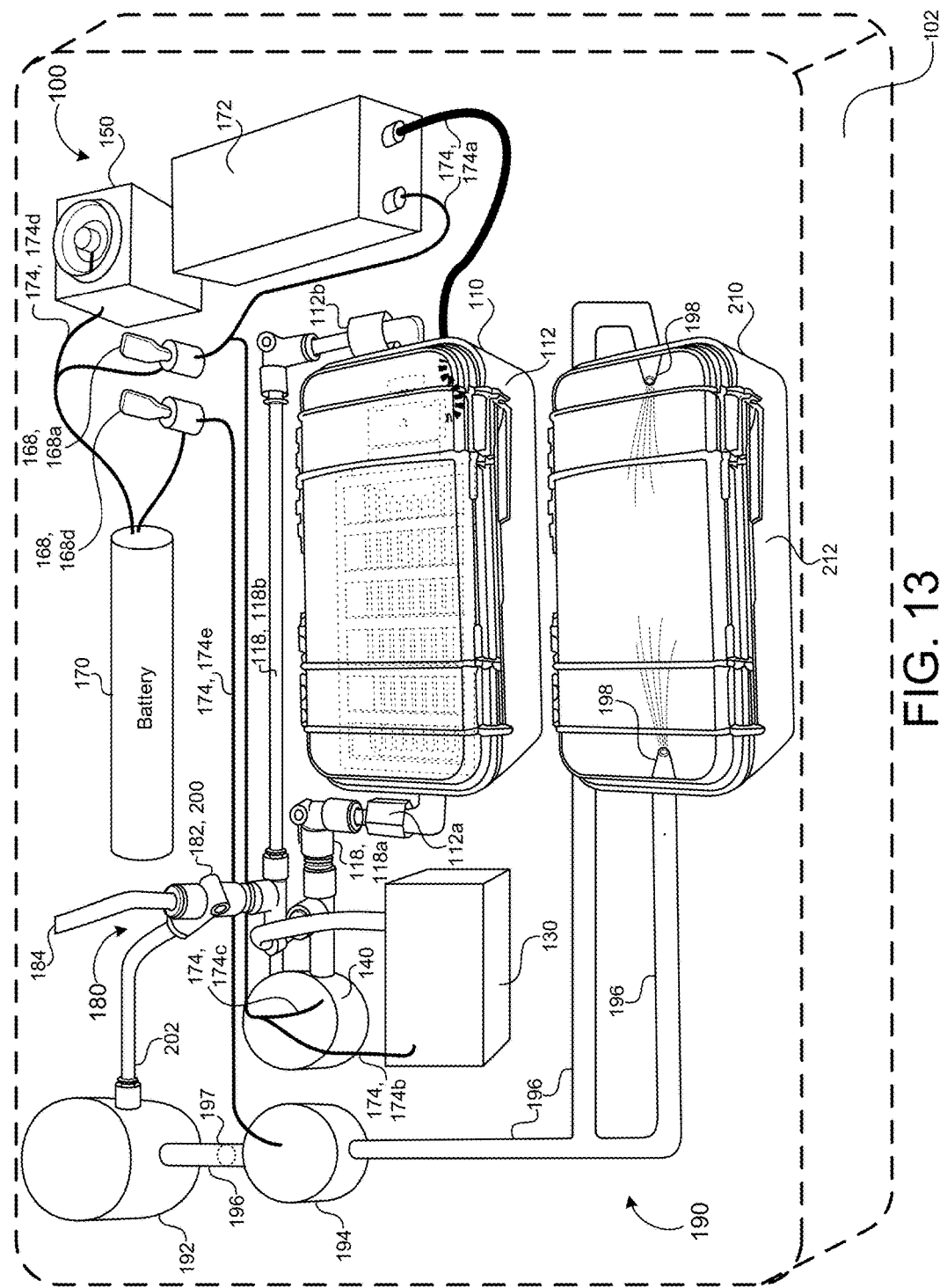
FIG. 13 is a perspective view of an example sterilization system having a pre-wash system.
Figure 14:
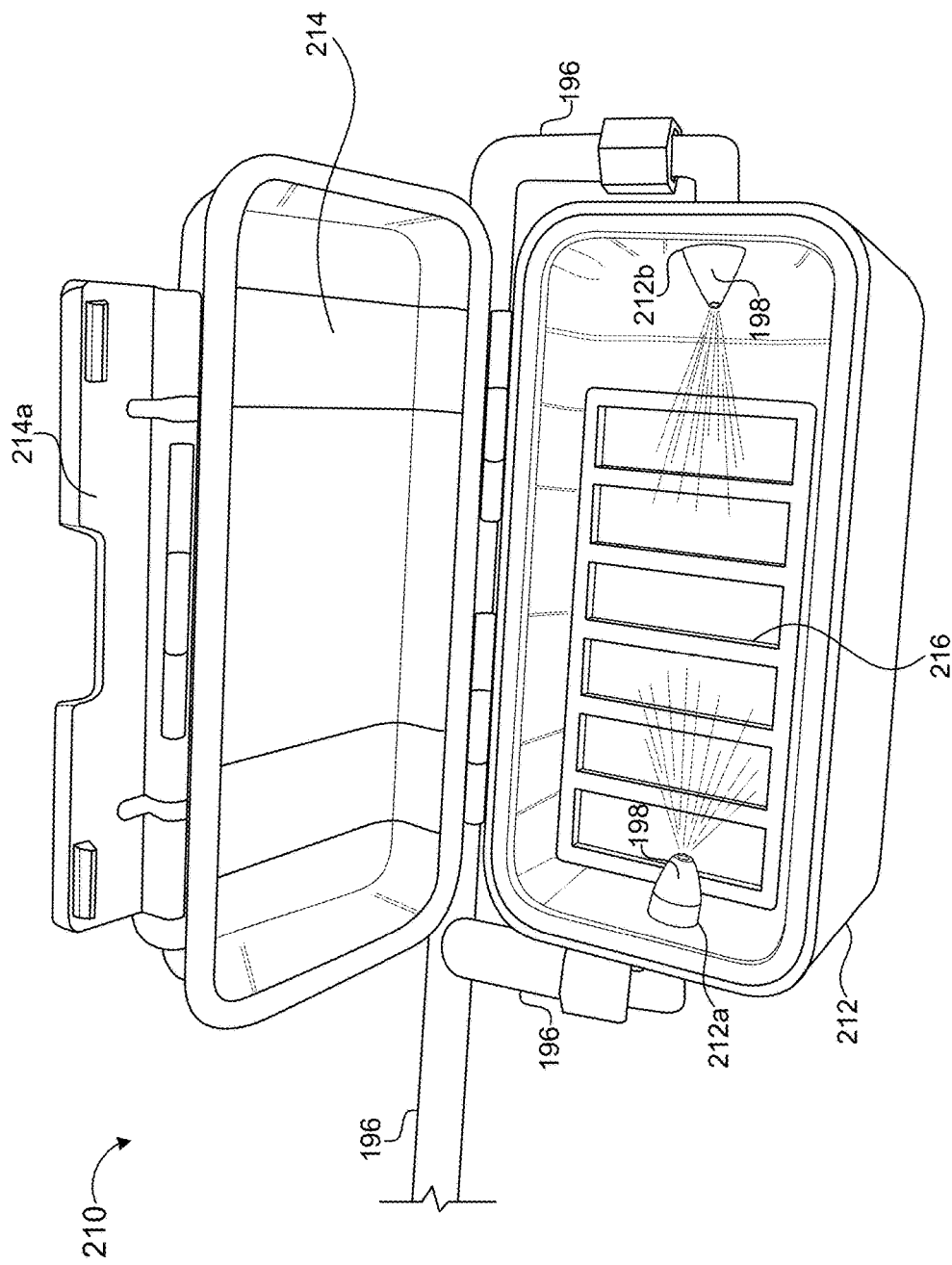
FIG. 14 is a perspective view of an example rinsing chamber.

Referring specifically to FIGS. 13-14, in some implementations of the sterilization system 100, the rinsing system 190 may further include a rinsing chamber. Similar to the implementation shown in FIG. 12, the implementation of FIGS. 13-14 may be utilized to effectuate a pre-wash cycle or can be utilized after the sterilization process within the sterilization chamber 110 to effectuate additional sterilization of the instrument or utensil.

The user deposits the instrument or utensil into the utensil tray 216 and closes the lid 214 of the rinsing chamber 210. A rinse fluid pump 194 initiates a flow of rinse fluid through the rinse fluid piping/tubing 196. The rinse fluid enters the rinsing chamber 210, and one or more nozzles 198 spray the rinse fluid at the utensil tray 216 to apply the rinse fluid to the instrument or utensil.

FIG. 14 illustrates an exemplary rinsing chamber 210, which includes a body 212 and a lid 214 received by the body 212. While the lid 214 is illustrated in FIG. 14 as being pivotally coupled to the body 212, the lid 214 may utilize an alternative design; it may be slidably attached to the body 212, uncoupled (e.g., freely attachable and removable from the body 212), or otherwise configured to move between a closed position and an open position. The lid 214 may be locked in the closed position during operation of rinsing system 190 using a locking mechanism 214a to prevent inadvertent or premature opening of the rinsing chamber 210 by a user. Alternatively, the lid 214 of the rinsing chamber 210 may be provided without a locking mechanism 214a.

The body 212 of the rinsing chamber 210 defines two openings 212a, 212b through which the rinse fluid piping/tubing 196 enters to the interior of the rinsing chamber 210. Within the interior of the rinsing chamber 210, the rinse fluid piping/tubing 196 terminates at two nozzles 198, which apply the rinse fluid to the instrument or utensil as desired. The quantity of nozzles 198 within the interior of the rinsing chamber 210 may vary from one to more than two depending of the desired spray pattern. While FIG. 14 illustrates a body 212 of the rinsing chamber 210 with two openings 212a, 212b, the quantity of openings may vary to correspond to the quantity of nozzles 198.

Referring again to FIGS. 12-16, the fluid reservoir 192 provides the rinse fluid to the rinse fluid pump 194. The rinse fluid piping/tubing 196 may include a filter screen, trough, or some other type of cleanout 197 to prevent suspended solids in the fluid reservoir 192 from reaching the rinse fluid pump 194. The power source 170 powers the rinse fluid pump 194 through a power line 174e.

Ozone disinfects the fluid in the fluid reservoir 192. Ozone-concentrated air from the sterilization chamber 110 travels to the fluid reservoir 192 through the ozone supply piping/tubing 202. FIGS. 12-13 illustrate a configuration in which the ozone-concentrated air comes from the exhaust system 180 piping/tubing. In other configurations, the ozone-concentrated air may be supplied to the fluid reservoir 192 by the air mover 140. Alternatively, ozone-concentrated air may travel to the fluid reservoir 190 directly from the ozone exhaust port 184, directly from the sterilization chamber 110, from any point on the gas piping/tubing 118, or from any other location with access to the ozone-concentrated air.

Ozone-concentrated air enters the fluid reservoir 192 and impregnates the fluid, which, in turn, sterilizes the fluid. Upon completion of the fluid sterilization, the rinse fluid pump 194 commences the rinsing process by supplying sterilized fluid from the fluid reservoir 192 to the one or more nozzles 198.

In the implementation of FIG. 12, the ozone supply valve 200, disposed on the ozone supply piping/tubing 202, moves between an open and a closed state. Either the user manually opens and closes the ozone supply valve 200 or an open/close signal supplied by the controller 150 through the communication line 152j automatically initiates opening and closing of the ozone supply valve 200. If the ozone supply valve 200 operates automatically upon receiving a signal from the controller 150, a power line 174g provides the ozone supply valve 200 with power from the power source 170. Accordingly, the ozone supply valve 200 remains open only during sterilization of the fluid in the fluid reservoir 192. In the implementation of FIG. 13, the ozone supply valve 200 and the exhaust valve 182 are illustrated as combined within a single three-way valve. This permits the ozone-concentrated air exhausted from the gas outlet piping/tubing 118b to travel to either the ozone exhaust port 184 or the fluid reservoir 192, depending upon the position of the three-way valve. In order to sterilize the fluid within the fluid reservoir 192, the positioning of the three-way valve would direct the ozone-concentrated air to the fluid reservoir 192 through the ozone supply piping/tubing 202. The three way valve can be manual, as shown in FIG. 13, or automatic, which would utilize control signals from the controller 150 through communication line 152j and power from the power source 170 through power line 174g. Although the implementation of FIG. 12 illustrates one configuration of the ozone supply valve 200 and FIG. 13 illustrates another configuration, each different configuration of the ozone supply valve 200 can be utilized in each implementation of the rinsing system 190, interchangeably.

Turning back to the general aspects of the rinsing system 190, the ozone generator 120 drives the sterilization of the fluid in the fluid reservoir 192 by generating the ozone-concentrated air utilized to impregnate and sterilize the fluid. To permit proper functioning of the ozone generator 120, the oxygen concentrator 130 also generates a gas rich in diatomic oxygen molecules and the air mover 140 circulates air through the sterilization chamber 110. During the sterilization process of the fluid in the fluid reservoir 192, the exhaust valve 182 remains in a closed position to direct sufficient ozone-concentrated air to the fluid reservoir 192.

The rinsing system 190 may include a sterilized fluid outlet 204. The user or the controller 150 directs the sterilized fluid outlet 204 to discharge sterilized fluid from the fluid reservoir 192 for external use by the user. Although the implementation of FIG. 12 includes a sterilized fluid outlet 204 and the implementation of FIG. 13 does not include a sterilized fluid outlet 204, either implementation—depending upon the needs of the user—could include or not include a sterilized fluid outlet 204.

In some implementations, the fluid reservoir 192, the rinse fluid pump 194, the rinse fluid piping/tubing 196, the ozone supply valve 200, and the ozone supply piping/tubing 202 are disposed within the portable case 102 of the sterilization system 100. If the rinsing system 190 includes a rinsing chamber 210, the rinsing chamber 210 may also disposed within the portable case 102.

In some implementations, the rinsing system 190 includes a fluid reservoir 192 for the sterilization of fluid, but does not include a rinse fluid pump 194, one or more nozzles 198, or a rinsing chamber 210. In these implementations, the user submerges the utensil or instrument in the fluid reservoir 192 to remove bio burden before inserting the utensil or instrument into the utensil tray 116 for sterilization. Such implementations optionally include a sterilized-fluid outlet 204.

As illustrated in FIG. 12, the sterilization chamber 110 optionally houses a debris scraper 116a. During the pre-wash cycle, bio burden may accumulate on the utensil tray 116. The debris scraper 116a removes bio burden from the utensil tray 116. FIG. 12 illustrates an automatic debris scraper 116a that receives power from power source 170 through a power line 174f and a signal to operate from the controller 150 through communication line 152k. Alternatively, the design of the debris scraper 116a may allow for manual operation only. In these implementations including a manual debris scraper 116a, the debris scraper 116a may be attached within the sterilization chamber 110 or may be stored elsewhere within the portable case 102.

In the implementation of FIG. 14, the rinsing chamber 210 is shown without a debris scraper 116a. However, similar to the sterilization chamber 110 in the implementation of FIG. 12, the rinsing chamber 210 may be provided with a manual or an electric debris scraper 116a to clean bio burden from the utensil tray 216 within the rinsing chamber 210.

Figure 15:
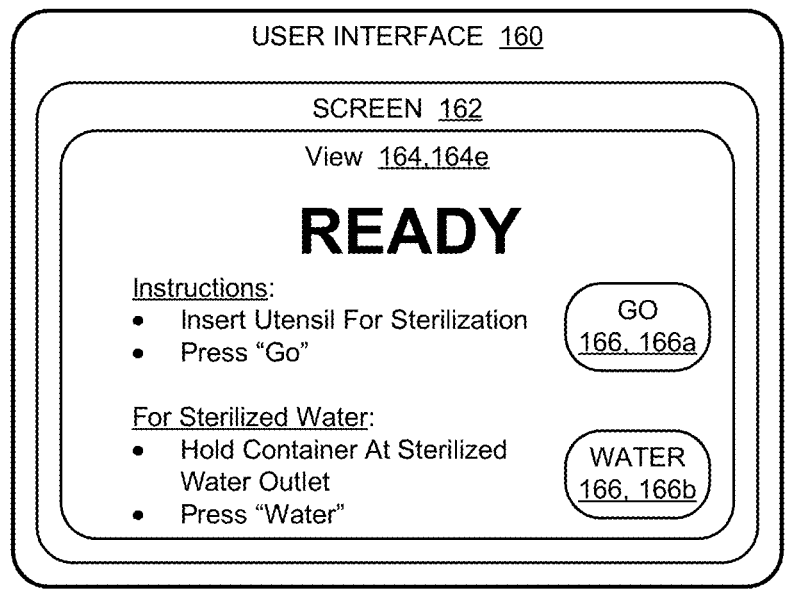
FIG. 15 is a schematic view of an example user interface associated with a sterilization system that includes a pre-wash system.

FIG. 15 illustrates an example ready view 164e shown on the screen 162 of the user interface 160 for a sterilization system 100 that includes a rinsing system 190. To begin the pre-wash and sterilization processes, the user presses a 'GO' button 166a. To receive sterilized fluid, which may consist of water or some other fluid, from the sterilized fluid outlet 204, the user presses a 'WATER' button 166b.

In alternative implementations, the user interface 160 optionally provides the user with an option to initiate the sterilization process without the pre-wash process or to initiate the pre-wash process without the sterilization process.

Figure 16:
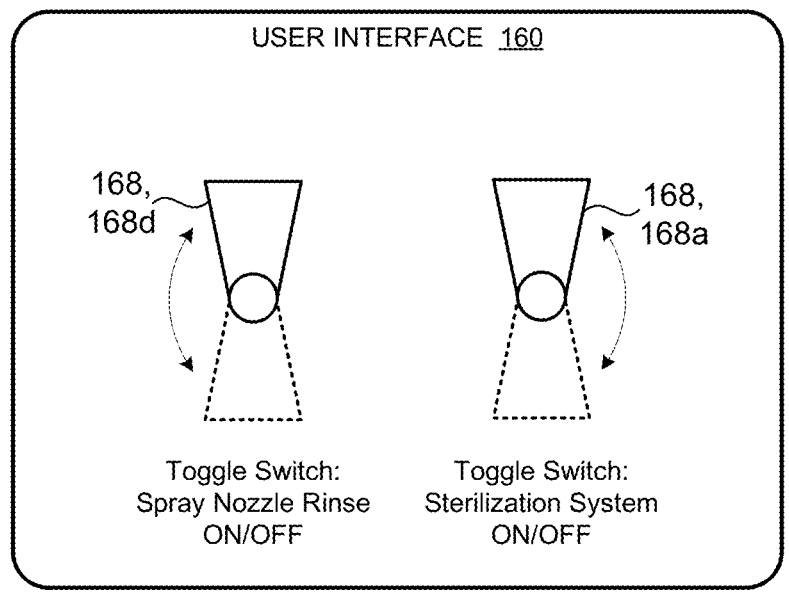
FIG. 16 is a schematic view of an example user interface having two on/off switches associated with a sterilization system that includes a prewash system.

Referring to FIG. 16, in some implementations, the user interface 160 includes one or more on/off switches 168. FIG. 16 illustrates an example user interface 160 with a first on/off switch 168d to initiate the pre-wash process and a second on/off switch 168a to initiate the sterilization process. Other alternative implementations optionally include one or more switches allowing the user to control different processes or components of the sterilization system 100 or, in particular, of the rinsing system 190.

Figure 17:
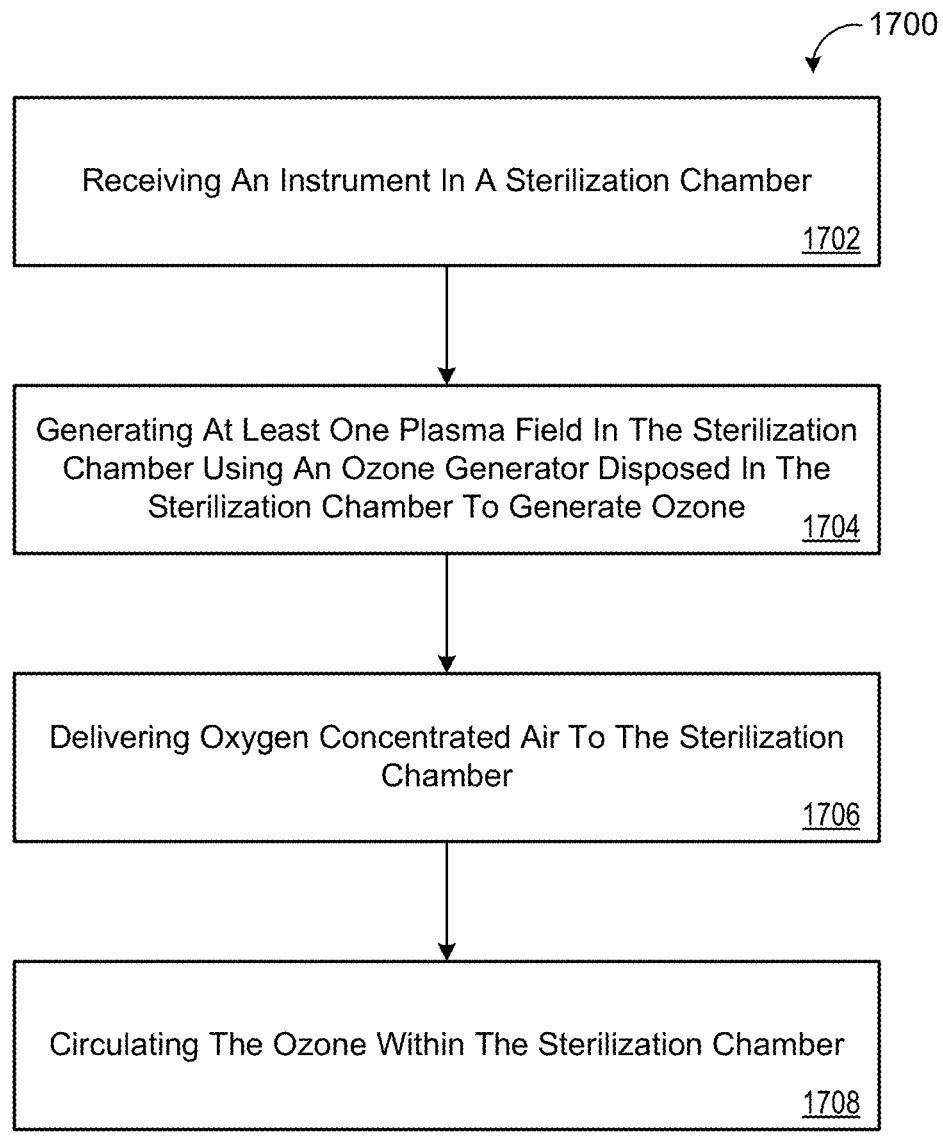
FIG. 17 is a schematic view of an exemplary arrangement of operations for a method of sterilizing an instrument.

FIG. 17 illustrates an exemplary arrangement of operations for a method 1700 of sterilizing an instrument. At block 1702, the method 1700 includes receiving an instrument in a sterilization chamber 110. At block 1704, the method 1700 includes generating at least one plasma field in the sterilization chamber 110 using an ozone generator 120 disposed in the sterilization chamber 110 to generate ozone. At block 1706, the method 1700 includes delivering oxygen-concentrated air to the sterilization chamber 110 (e.g., via an oxygen concentrator 130). At block 1708, the method 1700 includes circulating the ozone within the sterilization chamber 110 (e.g., via an air mover 140).

A number of implementations have been described. Nevertheless, it will be understood that various modifications may be made without departing from the spirit and scope of the disclosure. Accordingly, other implementations are within the scope of the following claims.

What is claimed is:

1. A sterilizer comprising:
a sterilization chamber having a gas inlet and a gas outlet;
an ozone generator housed by the sterilization chamber, the ozone generator generating at least one plasma field in the sterilization chamber and producing ozone-concentrated air within the sterilization chamber;
an air mover in fluid communication with the sterilization chamber and circulating air through the sterilization chamber and recirculating a portion of the ozone-concentrated air from the gas outlet of the sterilization chamber;

an oxygen concentrator in fluid communication with the sterilization chamber and located upstream of the gas inlet of the sterilization chamber, the oxygen concentrator delivering oxygen-concentrated air to the sterilization chamber; and a controller in communication with the ozone generator, the air mover, and the oxygen concentrator, wherein at the gas inlet of the sterilization chamber, the oxygen-concentrated air delivered from the oxygen concentrator mixes with the portion of ozone-concentrated air recirculated from the gas outlet of the sterilization chamber.

2. The sterilizer of claim 1, further comprising a power source in electrical communication with the ozone generator, the air mover, the oxygen concentrator, and the controller.

3. The sterilizer of claim 1, further comprising a timer used to activate and deactivate at least one of the ozone generator, the air mover, or the oxygen concentrator to maintain a threshold ozone level within the sterilization chamber.

4. The sterilizer of claim 1, wherein the controller controls ozone generation by pulsing power feed to the ozone generator, maintaining an air recirculation rate of the air mover to be between about 4 L/min and about 6 L/min, and maintaining an oxygen concentration of the oxygen concentrator to be at least 75% to maintain a threshold ozone level of about 4000 ppm within the sterilization chamber.

5. The sterilizer of claim 1, wherein the controller comprises a toggle switch controlling activation and deactivation of at least one of the ozone generator, the air mover, or the oxygen concentrator.

6. The sterilizer of claim 1, further comprising a utensil tray removably housed by the sterilization chamber.

7. The sterilizer of claim 1, further comprising an ozone meter in communication with the controller and measuring an ozone concentration in the sterilization chamber.

8. The sterilizer of claim 1, further comprising an oxygen concentration meter in communication with the controller and measuring an oxygen concentration within the sterilization chamber.

9. The sterilizer of claim 1, further comprising an air flow meter in communication with the controller and measuring a flow rate of the air circulated by the air mover.

10. The sterilizer of claim 1, wherein the controller utilizes a measurement from at least one of an ozone meter, an oxygen meter, and an air flow meter to change at least one operating parameter of at least one of the ozone generator, the air mover, and the oxygen concentrator.

11. The sterilizer of claim 1, further comprising a display in communication with the controller, the display displaying information associated with operation of the sterilizer.

12. The sterilizer of claim 1, further comprising:
an exhaust meter in fluid communication with the sterilization chamber and in electrical communication with the controller, the exhaust meter measuring at least one of an exhaust flow of gas out of the sterilization chamber or an ozone concentration of the exhaust flow of gas, wherein the controller triggers an alarm when the ozone concentration of the exhaust flow of gas is greater than a threshold ozone concentration.

13. The sterilizer of claim 1, further comprising a case housing the sterilization chamber, the air mover, the oxygen concentrator, and the controller.

14. The sterilizer of claim 1, further comprising an oxygen meter in communication with the controller and measuring an oxygen concentration of the oxygen-concentrated air delivered from the oxygen concentrator.

15. A sterilizer comprising:
a sterilization chamber;
an ozone generator housed by the sterilization chamber, the ozone generator generating at least one plasma field in the sterilization chamber;
an air mover in fluid communication with the sterilization chamber and circulating air through the sterilization chamber;
an oxygen concentrator in fluid communication with the sterilization chamber and delivering oxygen-concentrated air to the sterilization chamber;
a controller in communication with the ozone generator, the air mover, and the oxygen concentrator;
one or more spray nozzles disposed in the sterilization chamber;
a pump in fluid communication with the one or more spray nozzles; and
a fluid reservoir in fluid communication with the pump,
wherein the fluid reservoir is in fluid communication with the sterilization chamber, the pump circulating a rinse fluid between the fluid reservoir and the sterilization chamber.

16. The sterilizer of claim 15, further comprising a valve in fluid communication with the air mover, the valve moving between a closed state and an open state that directs ozone generated by the ozone generator to the fluid reservoir.

17. The sterilizer of claim 16, wherein the valve comprises:
a valve body defining a port; and
a valve seat disposed in the valve body, the valve seat moving between a closed position seated against the port and an open position spaced from the port when the port receives a connector stud.

18. A sterilizer comprising:
a sterilization chamber;
an ozone generator housed by the sterilization chamber, the ozone generator generating at least one plasma field in the sterilization chamber;
an air mover in fluid communication with the sterilization chamber and circulating air through the sterilization chamber;
an oxygen concentrator in fluid communication with the sterilization chamber and delivering oxygen-concentrated air to the sterilization chamber;
a controller in communication with the ozone generator, the air mover, and the oxygen concentrator;
a rinsing chamber;
one or more spray nozzles disposed in the rinsing chamber;
a pump in fluid communication with the one or more spray nozzles; and
a fluid reservoir in fluid communication with the pump.

19. The sterilizer of claim 18, wherein the fluid reservoir is in fluid communication with the rinsing chamber, the pump circulating a rinse fluid between the fluid reservoir and the sterilization chamber.

* * * * *